United States Patent
Kankan et al.

(10) Patent No.: US 8,716,476 B2
(45) Date of Patent: May 6, 2014

(54) PROCESS FOR THE PREPARATION OF ALFUZOSIN HYDROCHLORIDE

(75) Inventors: Rajendra Narayanrao Kankan, Maharashtra (IN); Dharmaraj Ramachandra Rao, Maharashtra (IN); Dilip Birari, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 12/671,418

(22) PCT Filed: Aug. 1, 2008

(86) PCT No.: PCT/GB2008/002632
§ 371 (c)(1),
(2), (4) Date: Jun. 22, 2010

(87) PCT Pub. No.: WO2009/016387
PCT Pub. Date: Feb. 5, 2009

(65) Prior Publication Data
US 2010/0256370 A1    Oct. 7, 2010

(30) Foreign Application Priority Data
Aug. 2, 2007  (IN) .......................... 1493/MUM/2007

(51) Int. Cl.
*C07D 239/95*    (2006.01)
(52) U.S. Cl.
USPC ....................................................... 544/291
(58) Field of Classification Search
USPC ....................................................... 544/291
See application file for complete search history.

(56) References Cited

U.S. PATENT DOCUMENTS

| | | |
|---|---|---|
| 4,315,007 A | 2/1982 | Manoury |
| 5,545,738 A | 8/1996 | Borrega et al. |
| 2007/0066824 A1 | 3/2007 | Anumula et al. |
| 2007/0105880 A1 | 5/2007 | Sadanand et al. |

FOREIGN PATENT DOCUMENTS

| | | |
|---|---|---|
| GB | 2231571 A | 11/1990 |
| WO | 2006090268 A2 | 8/2006 |
| WO | 2007069050 A2 | 6/2007 |
| WO | 2007074364 A1 | 7/2007 |
| WO | 2008114272 A2 | 9/2008 |
| WO | 2009016387 A2 | 2/2009 |
| WO | 2009016387 A3 | 2/2009 |

OTHER PUBLICATIONS

Foreign communication from the priority application—International Search Report and Written Opinion, PCT/GB2008/002632, May 19, 2009, 14 pages.
Foreign communication from the priority application—International Preliminary Report on Patentability, PCT/GB2008/002632, Feb. 11, 2010, 8 pages.
Foreign communication from a related counterpart application—Japanese Office Action with translation, JP Application No. 2010-518741, Jul. 25, 2013, 8 pages.
Foreign communication from a related counterpart application—European Examination Report, EP Application No. 08 788 253.6, Aug. 29, 2013, 4 pages.
Chou, Wen-Chin, et al., "HMDS-Promoted in Situ Amidation Reactions of Carboxylic Acids and Amines," Tetrahedron Letters, 1999, pp. 3419-3422, vol. 40, Elsevier Science Ltd.

*Primary Examiner* — Brian McDowell
(74) *Attorney, Agent, or Firm* — Conley Rose, P.C.; Rodney B. Carroll

(57) ABSTRACT

A process for preparing alfuzosin or a salt thereof comprising: (a) condensing 4-amino-2-chloro-6,7-dimethoxyquinazoline with 3-methylaminopropionitrile in the presence of a polar aprotic solvent selected from the group consisting of diglyme, dimethyl formamide, t-butanol, hexamethylphosphoramide or mixtures thereof to form N-(4-amino-6,7-dimethoxyquinazol-2-yl)-N-methyl-2-cyanoethylamine (b) hydrogenating the N-(4-amino-6,7-dimethoxyquinazol-2-yl)-N-methyl-2-cyanoethylamine using a hydrogenating agent under a pressure of less than 10 $kg/cm^2$ to form N-(4-amino-6,7-dimethoxyquinazol-2-yl)-N-methylpropylenediamine and optionally converting the N-(4-amino-6,7-dimethoxyquinazol-2-yl)-N-methylpropylenediamine to an acid addition salt thereof; and (c) converting tetrahydrofuroic acid to an intermediate form and condensing the intermediate form with the N-(4-amino-6,7-dimethoxyquinazol-2-yl)-N-methylpropylenediamine or with the acid addition salt to yield alfuzosin base, and optionally converting alfuzosin base to a salt of alfuzosin.

27 Claims, No Drawings

PROCESS FOR THE PREPARATION OF ALFUZOSIN HYDROCHLORIDE

CROSS-REFERENCE TO RELATED APPLICATIONS

This application is a filing under 35 U.S.C. 371 of International Application No. PCT/GB2008/002632 filed Aug. 1, 2008, entitled "Process for the Preparation of Alfuzosin Hydrochloride," claiming priority of Indian Patent Application No. 1493/MUM/2007 filed Aug. 2, 2007, which applications are incorporated by reference herein in their entirety.

FIELD OF THE INVENTION

The present invention relates to an improved process for the preparation of alfuzosin hydrochloride.

BACKGROUND OF THE INVENTION

Alfuzosin hydrochloride has the chemical name N-[3-[(4-Amino-6,7-dimethoxy-2-quinazolinyl)methylamino]propyl] tetrahydro-2-furancarboxamide hydrochloride and has the structural formula as Formula I.

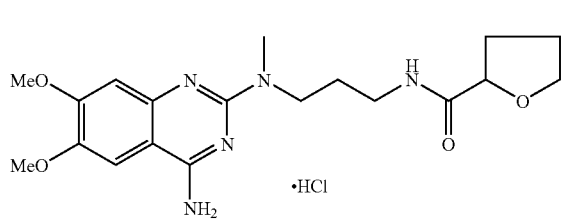

Alfuzosin hydrochloride is an antagonist of the α-adrenergic receptor, and is useful as an antihypertensive agent and dysuria treatment agent.

The earliest known synthesis of alfuzosin hydrochloride, by Manoury et al, is described in U.S. Pat. No. 4,315,007. The synthetic method employed is depicted in the following reaction scheme 1.

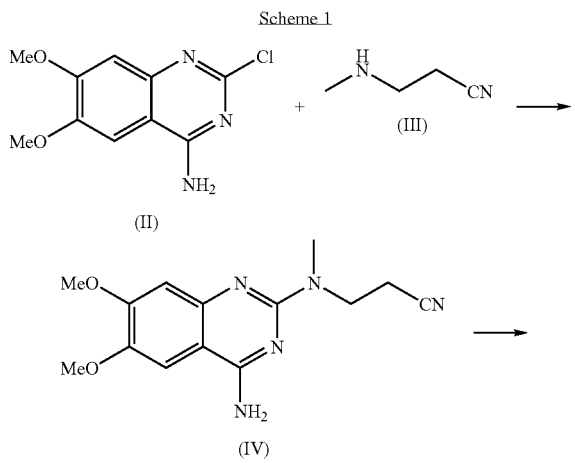

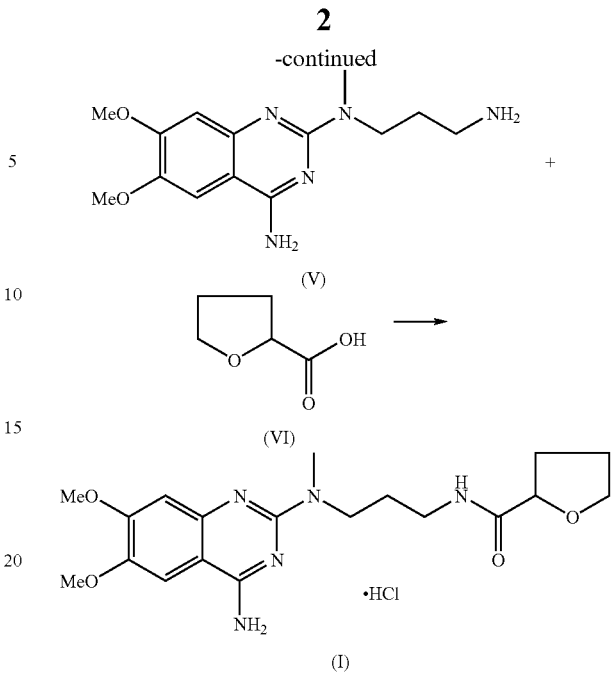

The patent 007' teaches the preparation of alfuzosin or a salt thereof by reacting 4-amino-2-chloro-6,7-dimethoxy quinazoline of formula (II) with 3-methylaminopropionitrile of formula (III) in the presence of isoamyl alcohol to obtain N-(4-amino-6,7-dimethoxyquinazol-2-yl)-N-methyl-2-cyanoethylamine of formula (IV) which is further hydrogenated in the presence of Raney-Nickel using 15% ammoniacal ethanol by applying 80 Kg pressure at 70° C. for 96 hours to obtain N-(4-amino-6,7-dimethoxyquinazol-2-yl)-N-methylpropylenediamine of formula (V) which is then converted to the hydrochloride salt. The obtained N-(4-amino-6,7-dimethoxyquinazol-2-yl)-N-methylpropylenediamine hydrochloride is then treated with carbonyldiimidazole-activated tetrahydrofuroic acid by adding a diamine compound in the presence of carbonyldiimidazole to obtain alfuzosin base which is then converted into alfuzosin hydrochloride salt.

The process has many disadvantages, for example:
a) The use of isoamyl alcohol as a reaction solvent is irritating to the skin, eyes and respiratory system. Also, it results in an extended reaction time consequently leading to formation of 10-12% of one of the potential impurities termed herein as "alfuzosin impurity A"

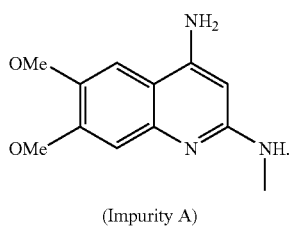 [SMILES: CNc1cc(N)c2cc(OC)c(OC)cc2n1]

(Impurity A)

This impurity carries over to the subsequent steps for preparing alfuzosin, making it more difficult to isolate a pure product, hence the process is not viable industrially.
b) The use of the high pressure of 80 kg/cm² and dry conditions for a long duration in the hydrogenation, makes the process unsuitable for industrial scale up. The yield and the purity of the end product obtained by using the stated procedure in accordance with scheme I is therefore greatly compromised. This leads to an overall increase in the handling and production costs.

A refinement of the above process is described in US2007/0105880 ("'880"). Nevertheless, the process of '880 suffers from several significant drawbacks. For example, the N-(4-amino-6,7-dimethoxyquinazol-2-yl)-N-methyl-2-cyanoethylamine of formula (IV) is hydrogenated at a high pressure of 10-15 kg using ammoniacal ispropanol solution. This reaction is carried out under dry conditions. Under the reaction conditions described in '880, the compound N-(4-amino-6,7-dimethoxyquinazol-2-yl)-N-methylpropylenediamine of formula (V) does not precipitate out; a seed is required to precipitate compound (V), which makes the process cumbersome and non-reproducible. Further, '880 claims the use of a base for preparation of N-(4-amino-6,7-dimethoxyquinazol-2-yl)-N-methyl-2-cyanoethylamine of formula (IV). However, there is no example disclosing the use of any base in the reaction.

The alfuzosin obtained in the next step on '880 by reaction of the compound of formula (V) with carbonyldiimidazole-activated tetrahydrofuroic acid, is impure in nature and hence needs repetitive crystallization before converting it into the hydrochloride salt.

Processes for the preparation of alfuzosin and its pharmaceutically acceptable salts have also been described in U.S. Pat. No. 5,545,738, GB Patent No. 2231571, and US2007/0066824. U.S. Pat. No. 5,545,738 discloses a process for preparing the dihydrate form of alfuzosin hydrochloride. GB 2231571 discloses a process for preparing alfuzosin or salts thereof comprising reacting an isothiourea derivative with an amine and cyclising the resulting product to form alfuzosin. US2007/0066824 discloses a process for preparing salts of alfuzosin comprising a) esterifying tetrahydrofuroic acid; b) condensing the esterified product of step a) with 3-methyl amino propylene diamine to get $N_1$-methyl-$N_2$-tetrahydrofuroyl propylene diamine; c) condensing $N_1$-methyl-$N_2$-tetrahydrofuroyl propylene diamine with 4-amino-2-chloro-6,7-dimethoxyquinozoline to yield alfuzosin free base; d) treatment of alfuzosin free base of with a pharmaceutically acceptable acid to afford a pharmaceutically acceptable acid addition salt of alfuzosin.

The processes described in the above patents involve multiple steps and involve the formation of an unstable ester as an intermediate, which leads to decreased yield and purity of the product.

Therefore, there exists a need for a more economical and efficient method of making alfuzosin which is suitable for industrial scale up.

The present invention provides an improved process for synthesis of alfuzosin which avoids all the disadvantages associated with the prior art processes.

OBJECTS OF THE INVENTION

One object of the present invention is to provide an improved process for preparing alfuzosin hydrochloride.

Another object of the present invention is to provide a purification method to obtain high purity alfuzosin hydrochloride.

Yet another object of the present invention is to provide a process for preparing alfuzosin hydrochloride which is simple, economical and suitable for industrial scale up.

SUMMARY OF THE INVENTION

According to a first aspect of the present invention, there is provided a process for preparing N-(4-amino-6,7-dimethoxyquinazol-2-yl)-N-methyl-2-cyanoethylamine (IV) or a salt thereof comprising condensing 4-amino-2-chloro-6,7-dimethoxy quinazoline (II) with 3-methylaminopropionitrile (III) in the presence of a polar aprotic solvent selected from the group consisting of diglyme, dimethyl formamide, t-butanol, hexamethylphosphoramide or mixtures thereof, and optionally converting N-(4-amino-6,7-dimethoxyquinazol-2-yl)-N-methyl-2-cyanoethylamine (IV) to a salt thereof.

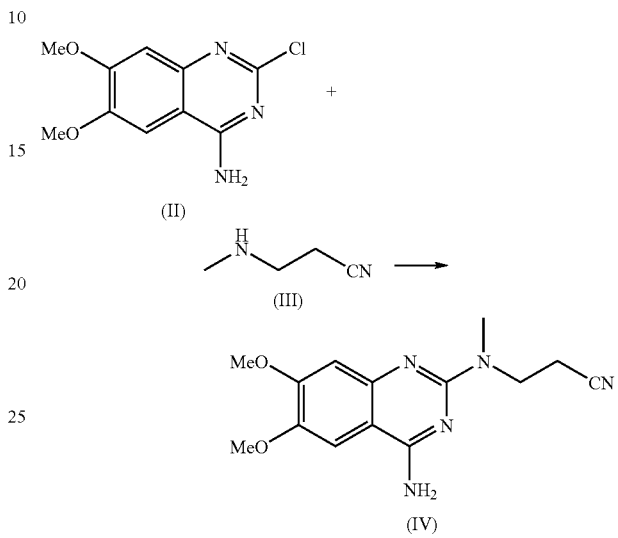

In an embodiment, the solvent is diglyme, t-butanol or a mixture thereof. The condensation reaction may be carried out in the presence or absence of a base such as an organic or inorganic base. Preferably, the condensation reaction is carried out in the absence of a base. The N-(4-amino-6,7-dimethoxyquinazol-2-yl)-N-methyl-2-cyanoethylamine (IV) prepared according to this process may have a purity greater than 95%, preferably greater than 98%. In a particularly preferred embodiment, the use of a mixture of diglyme- and t-butanol reduces the amount of impurity A to about 2%, compared to an amount of around 12% according to the prior art process.

In an embodiment, the N-(4-amino-6,7-dimethoxyquinazol-2-yl)-N-methyl-2-cyanoethylamine (IV) is converted into an acid addition salt of the formula (IVa) in the presence of an acid HA

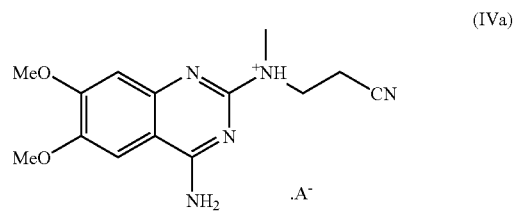

wherein $A^-$ is an anion. The acid may be an inorganic acid or organic acid.

According to a second aspect of the present invention, there is provided a process for preparing N-(4-amino-6,7-dimethoxyquinazol-2-yl)-N-methyl propylenediamine (V) or a salt thereof comprising hydrogenating N-(4-amino-6,7-dimethoxyquinazol-2-yl)-N-methyl-2-cyanoethylamine (IV) using hydrogenating agent, for example Raney Nickel, under a pressure of less than 10 kg/cm² and optionally converting the N-(4-amino-6,7-dimethoxyquinazol-2-yl)-N-methyl propylenediamine (V) to a salt thereof.

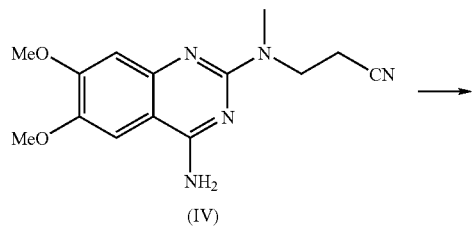

(IV)

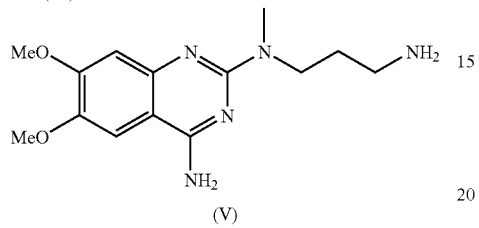

(V)

Preferably, the pressure is around 5-6 kg/cm².

In an embodiment, the hydrogenation is carried out in the presence of an alcohol and an aqueous ammonia solution. The alcohol may be methanol or ethanol, for example denatured ethanol. It is advantageous to use "wet" conditions, i.e. aqueous ammonia rather than dry ammonia. In US'007 and US'880, "dry" conditions are used. More specifically, the hydrogenation processes in these prior art patents use ammoniacal isopropanol or ammoniacal ethanol, which is dry ammonia gas purged in either isopropanol or ethanol. The use of wet conditions make the process of the present invention more suitable for industrial application.

In an embodiment, the hydrogenation reaction takes place over a period of time ranging from about 2 hours to about 10 hours, preferably from about 2 hours to about 5 hours. Most preferably, the reaction takes place over a period of time of about 2 hours. In US'880, the reaction time is 6 hours.

In an embodiment, the N-(4-amino-6,7-dimethoxyquinazol-2-yl)-N-methyl propylenediamine (V) is converted to an acid addition salt (Va)

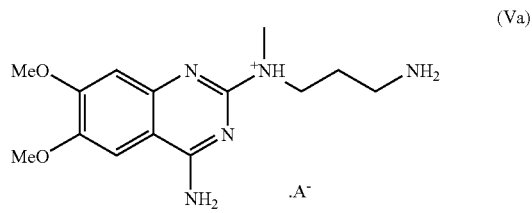

(Va)

wherein A⁻ is an anion. The acid may be an inorganic acid or organic acid.

In an embodiment, the N-(4-amino-6,7-dimethoxyquinazol-2-yl)-N-methyl-2-cyanoethylamine (IV) is prepared according to a process described in the first aspect of the invention.

According to a third aspect of the present invention, there is provided a process for preparing alfuzosin free base or alfuzosin hydrochloride comprising converting tetrahydrofuroic acid (VI) to an intermediate form (VII)

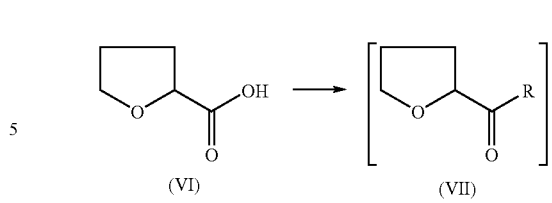

wherein R is: (i) a halo group; (ii) $OR_1$ wherein $R_1$ is a silyl group having the formula

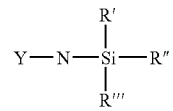

wherein R', R" and R"' are the same or different and are selected from hydrogen, optionally substituted $C_1$-$C_6$ alkyl, optionally substituted $C_2$-$C_6$ alkenyl; Y is selected from hydrogen, $C_1$-$C_6$ alkyl, $C_2$-$C_6$ alkenyl and silyl, preferably substituted silyl; (iii) $OR_2$ wherein $R_2$ is a $C_1$ to $C_4$ allyl group; or (iv) $OR_3$, wherein $R_3$ is either (i) succinimide and intermediate form (VII) is intermediate ester (VIIc)

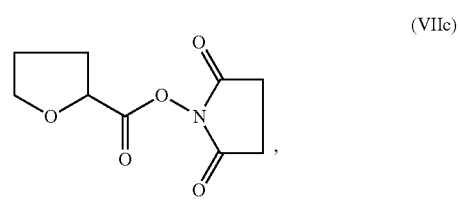 [SMILES: O=C(ON1C(=O)CCC1=O)C1CCCO1]

(VIIc)

or (ii) asparagine, and condensing the intermediate form (VII) with N-(4-amino-6,7-dimethoxyquinazol-2-yl)-N-methyl propylenediamine (V) or with acid addition salt (Va) to yield alfuzosin base and optionally converting alfuzosin base to alfuzosin hydrochloride (I), wherein the process is carried out without isolating the intermediate of formula (VII). In the context of the present invention, the term "without isolation" means that the product being referred to as not being isolated is not isolated as a solid, for example it is not isolated from the reaction mass and dried to form a solid. Thus, "without isolation" may mean that the product remains in solution and is then used directly in the next synthetic step, or it may mean that solvent is substantially removed from a solution of the product such that the product is present as a residue, but not as a solid.

Other salts of alfuzosin may be prepared in the same way. Optionally, alfuzosin base is isolated. The isolated alfuzosin base may be converted to the hydrochloride salt of alfuzosin. Alternatively, alfuzosin base is not isolated before being converted to alfuzosin hydrochloride.

When R is a halo group, for example a chloro or bromo group, tetrahydrofuroic acid (VI) is treated with a halogenating agent; preferably a chlorinating agent, to yield tetrahydrofuroyl chloride (VIIa).

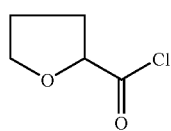

(VIIa)

Preferred chlorinating agents are, for example thionyl chloride, phosphorus oxychloride, phosphorus trichloride, phosphorus pentachloride, phosgene and oxalyl chloride. The chlorination is performed in a manner known to those skilled in the art. In general, it is preferred to heat the tetrahydrofuroic acid (VI) with the chlorinating agent, which will either be used neat or in a solution with a suitable solvent such as, for example toluene, methylenechloride, acetonitrile, tetrahydrofuran, diglyme, dimethylforamide or dioxane or the like. It is preferred to perform chlorination by refluxing with neat thionyl chloride, any excess of which can later be conveniently removed by evaporation.

When the intermediate is condensed with the diamine (V), the any residual chlorinating agent if first removed, as this would react with the diamine (V). If chlorination is performed in a solvent, then it is preferable to employ a high boiling point solvent, so that the chlorinating agent may be removed by evaporation.

In an embodiment, tetrahydrofuroic acid (VI) is converted to tetrahydrofuroyl chloride (VIIa), and a preferred method for preparing alfuzosin base or hydrochloride comprises reacting diamine (V) in situ with tetrahydrofuroyl chloride (VIIa) in the presence of an anhydrous solvent, i.e. without isolation of tetrahydrofuroyl chloride (VIIa). Optionally, a base, either organic or inorganic, may be added to the reaction mixture as an acid scavenger. The reaction rate may be increased by heating the reaction mass to the boiling point of the solvent.

When R is $OR_2$, wherein $R_2$ is a $C_1$ to $C_4$ alkyl group, $R_2$ may be methyl, ethyl, n-propyl, isopropyl, n-butyl or tertiary butyl. The formation of the intermediate (VII) may comprise esterifying tetrahydrofuroic acid (VI) with an alcohol of the formula $R_2OH$, wherein $R_2$ has the same meanings as given above, in the presence of an acid. The acid may be selected from the group consisting of acetic acid, sulfuric acid and nitric acid.

When R is $OR_1$ and $R_1$ is the silyl group defined above, the process for preparing alfuzosin may comprise reacting tetrahydrofuroic acid (VI) with diamine (V) in the presence of a silicon amine based on the silyl group of the formula.

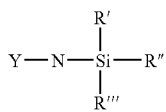

Thus, the silyl group is nitrogen-bonded to the oxygen of the $OR_1$ group. The term "$C_1$-$C_6$ alkyl" represents straight-chain or branched-chain alkyl having 1 to 6 carbon atoms. The term "silyl" represents —$SiH_3$. Silyl can be substituted with one or more substitutents such as $C_1$-$C_6$ alkyl and hydroxyl.

Optionally, the silicon amine is selected from alkali metal disilazane or alkali metal monosilazane. The alkali metal may be selected from lithium, sodium or potassium.

Preferably, the silicon amine used 1,1,1,3,3,3-hexamethyl-disilazane (HMDS).

The condensation reaction is preferably carried out under an inert atmosphere at a temperature ranging from 50 to 200° C. The process is preferably carried out for several hours until the condensation reaction completes.

Alternatively, the condensation reaction may be carried out by reacting tetrahydrofuroic acid (VI) with ethyl chloroformate in the presence of a base and a polar protic solvent.

When R is $OR_3$ and $R_3$ is either (i) succinimide and intermediate form (VII) is intermediate ester (VIIc)

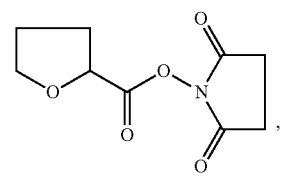

(VIIc)

or (ii) asparagine, $R_3$ is preferably succinimide and intermediate form (VII) is intermediate ester (VIIc).

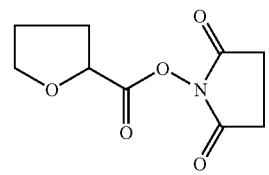

(VIIc)

The reaction may be carried out in the presence of a catalyst such as dimethylaminopyridine, using an organic solvent in an inert atmosphere. The ester (VIIc) may then be condensed with diamine (V) in a suitable organic solvent preferably dichloromethane using a suitable organic base or an inorganic base, suitably under an inert atmosphere to form alfuzosin base or hydrochloride. The condensation reaction may be carried out by isolating intermediate ester (VIIc). Preferably, the reaction is carried out without isolating ester (VIIc).

In an embodiment, the process involves reacting a solution of compound (VI) or (VII) with diamine compound (V) or vice versa in a solvent at a suitable temperature to yield alfuzosin. After completion of reaction, the mixture may be basified, extracted in a suitable solvent, neutralized, washed with water and dried. Alternatively, the solvent may be evaporated partially or completely to provide a residue or solution of alfuzosin base in a solvent. In a preferred embodiment, the residue of alfuzosin is dissolved in methanol and acidified with hydrochloric acid either as gas or as an aqueous solution or as alcoholic solution to yield alfuzosin hydrochloride.

The solid alfuzosin hydrochloride may be obtained by distilling the solvent under reduced pressure and adding an antisolvent to the residue of alfuzosin base in a solvent. Suitable antisolvents may be selected from esters or ethers. The alfuzosin hydrochloride may be isolated by filtration and may be purified further using known crystallization techniques.

Still another aspect of the present invention is to provide pharmaceutical composition containing a therapeutically effective amount of pure alfuzosin hydrochloride, along with one or more pharmaceutically acceptable carriers, diluents and excipients. Such pharmaceutical compositions are well known to those skilled in the art and processes for preparing them are also well known.

DETAILED DESCRIPTION OF THE INVENTION

In one embodiment, the present invention provides an improved process for the synthesis of alfuzosin hydrochloride as depicted in reaction scheme 2 below:

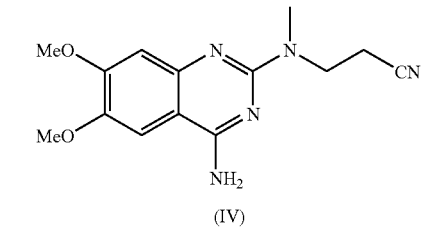

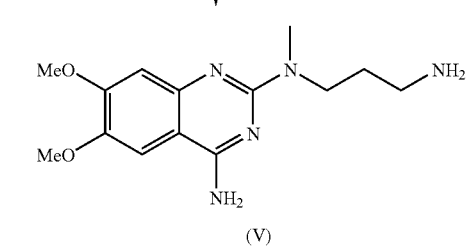

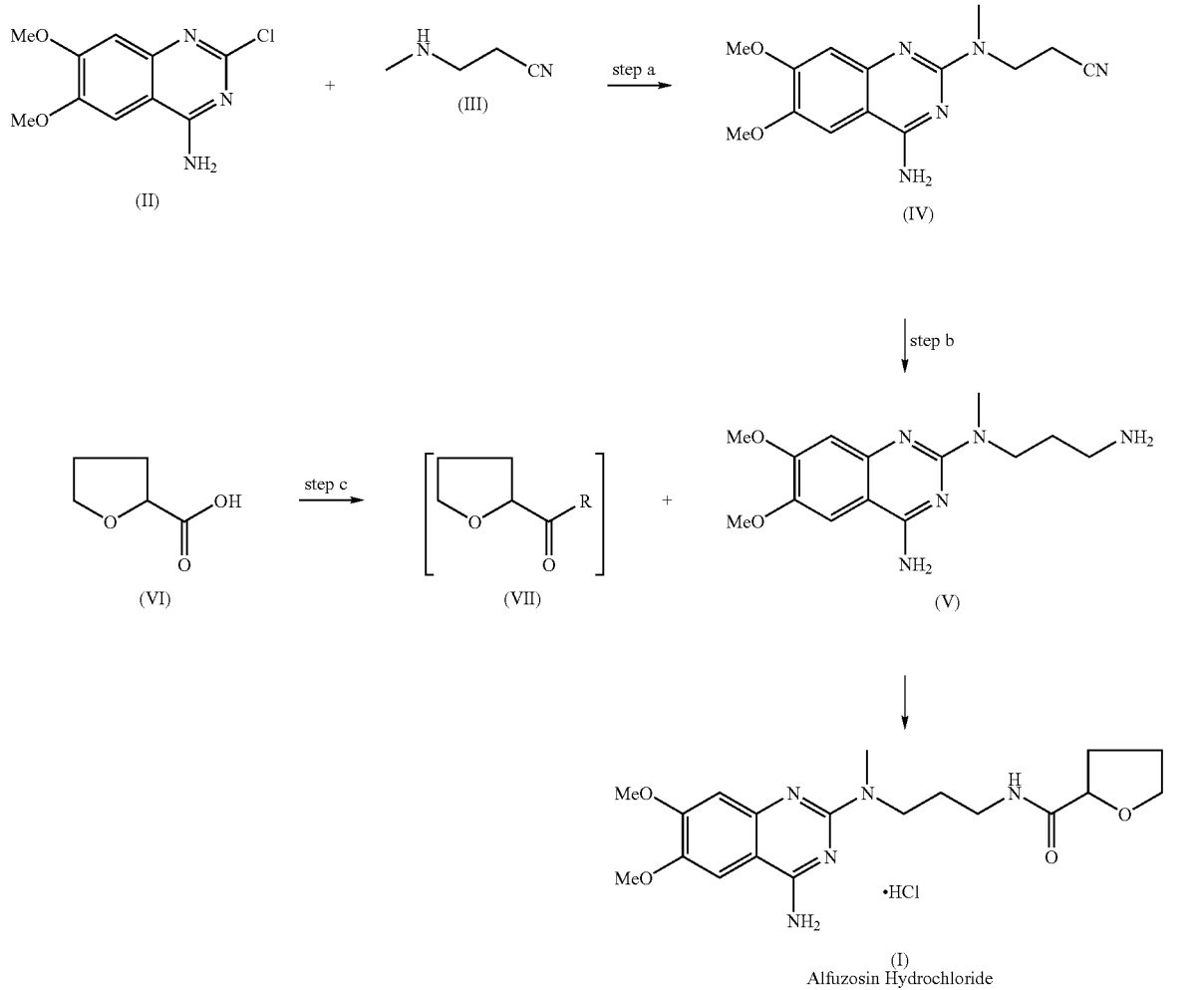

wherein R is as defined above.

In step a, 4-amino-2-chloro-6,7-dimethoxy quinazoline (II) is condensed with 3-methylaminopropionitrile (III) in the presence of a polar aprotic solvent to yield N-(4-amino-6,7-dimethoxyquinazol-2-yl)-N-methyl-2-cyanoethylamine (IV). Appropriate polar aprotic solvents are selected from the group consisting of diglyme, dimethyl formamide, t-butanol, or mixtures thereof. Preferred solvents for the reaction are diglyme, t-butanol or a mixture thereof, more preferably a mixture thereof. The solvents used in the process of present invention the reduce formation of "alfuzosin impurity A" to a level below 2% instead of 10-12% when the prior art process is followed. This consequently improves the yield, colour and purity of N-(4-amino-6,7-dimethoxyquinazol-2-yl)-N-methyl-2-cyanoethylamine (IV). Further the reaction may be carried out optionally in the presence of either organic or inorganic base. In an embodiment, the reaction is carried out without base. N-(4-amino-6,7-dimethoxyquinazol-2-yl)-N-methyl-2-cyanoethylamine (IV) prepared according to this embodiment and salts thereof may have purity greater than 95%, preferably greater than 98%.

The free base obtained may be optionally purified by converting into acid addition salt (IVa).

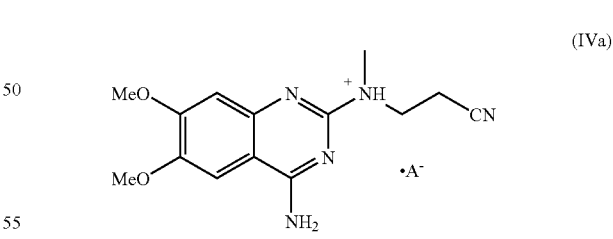

wherein $A^-$ is an anion. The anion corresponds to the acid used. The acid used may be selected from inorganic acids and organic acids and the like.

In step b, N-(4-amino-6,7-dimethoxyquinazol-2-yl)-N-methyl-2-cyanoethylamine (IV) is hydrogenated to yield N-(4-amino-6,7-dimethoxyquinazol-2-yl)-N-methyl propylenediamine (V). The reaction is carried out at pressure of less than 10 kg/cm², preferably at 5-6 kg/cm². The reaction does not require anhydrous conditions as reported in the prior art. The prior art teaches use of absolute ethanol or tetrahydrofuran which require dry ammonia gas or solution of dry ammonia gas either in ethanol or in isopropanol. In the process of present invention, the preferred solvent is denatured alcohol along with aqueous ammonia solution. The improved reaction condition reduces reaction hours from 96 hours to about 10 hours, preferably about 2 hours, making the process more feasible on an industrial scale. This forms another aspect of the present invention.

Optionally, N-(4-amino-6,7-dimethoxyquinazol-2-yl)-N-methyl propylenediamine (V) can be isolated as acid addition salt (Va)

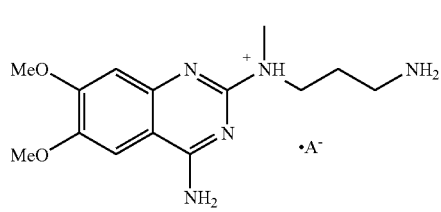

(Va)

In step c, tetrahydrofuroic acid (VI) is activated to an intermediate of formula (VII) and condensed with N-(4-amino-6,7-dimethoxyquinazol-2-yl)-N-methyl propylenediamine (V) or with acid addition salt (Va) to yield alfuzosin hydrochloride (I). Optionally, alfuzosin base can be isolated. Suitably, condensation is carried out without isolating intermediate of formula (VII).

In one embodiment, in step c, where R is a halo group, tetrahydrofuroic acid (VI) is treated with a halogenating agent; preferably a chlorinating agent, to yield tetrahydrofuroyl chloride (VIIa).

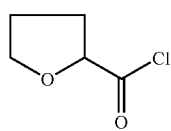

(VII a)

Preferred chlorinating agents are, for example thionyl chloride, phosphorus oxychloride, phosphorus trichloride, phosphorus pentachloride, phosgene and oxalyl chloride. The chlorination is performed in a manner known to those skilled in the art. In general, it is preferred to heat the tetrahydrofuroic acid (VI) with the chlorinating agent, which will either be used neat or in a solution with a suitable solvent such as, for example toluene, methylenechloride, acetonitrile, tetrahydrofuran, diglyme, dimethylforamide or dioxane or the like. It is preferred to perform chlorination by refluxing with neat thionyl chloride, any excess of which can later be conveniently removed by evaporation. It is essential to first remove any remaining chlorinating agent, as this would react with the diamine (V). If chlorination is done in a solvent, then it is preferable to employ a high boiling solvent, so that the chlorinating agent may be removed by evaporation.

When tetrahydrofuroic acid (VI) is converted to tetrahydrofuroyl chloride (VIIa), a preferred method for preparing alfuzosin hydrochloride is reacting diamine (V) in situ with an acid chloride (VIIa), by dissolving in a suitable anhydrous solvent. Optionally, a base, either organic or inorganic, may be added to the reaction mixture as an acid scavenger. The reaction rate may be increased by heating up to the boiling point of the solvent.

In another embodiment, in step c, $R_1$ is a hydroxy protective group, such as an ester group and the process to prepare alfuzosin comprises; esterifying tetrahydrofuroic acid (VI) with alcohol in the presence of an acid to form ester of formula (VIIb)

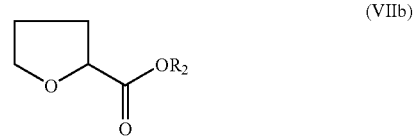

(VIIb)

wherein $R_2$ is $C_1$ to $C_4$ alkyl group and; condensing esterified intermediate without isolating it, with diamine (V) optionally in the presence of solvent. The alcohol suitable for the process is selected from $C_1$-$C_4$ alcohols like methanol, ethanol, butanol, isopropanol, n-propanol, tertiary butanol and the like. The acid used selected from the group comprising of acetic acid, sulfuric acid, nitric acid and the like.

In yet another embodiment, in step c, the process for preparing alfuzosin involves: reacting tetrahydrofuroic acid (VI) with diamine (V) in the presence of a silicon amine based on a silyl group of the formula

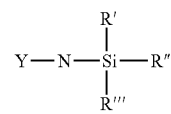

wherein R', R" and R'" are the same or different and are selected from hydrogen, optionally substituted $C_1$-$C_6$ alkyl, optionally substituted $C_2$-$C_6$ alkenyl; Y is selected from hydrogen, $C_1$-$C_6$ alkyl, $C_2$-$C_6$ alkenyl and optionally substituted silyl. Thus, in this embodiment, R is $OR_1$ and $R_1$ is the radical shown above. The term "$C_1$-$C_6$ alkyl" represents straight or branched-chain alkyl groups having 1 to 6 carbon atoms, for example methyl, ethyl, n-propyl, isopropyl, n-butyl, tertiary butyl, pentyl or hexyl. The term "$C_2$-$C_6$ alkenyl" represents straight or branched-chain alkenyl groups having 2 to 6 carbon atoms, such as ethenyl and n-propenyl. The term "silyl" represents —$SiH_3$. Silyl may be substituted with one or more substitutents such as $C_1$-$C_6$ alkyl and hydroxyl.

Optionally, the silicon amine may be selected from alkali metal disilazane or alkali metal monosilazane. The alkali metal may be selected from lithium, sodium or potassium. In the present invention, preferable silicon amine used is 1,1,1, 3,3,3-hexamethyldisilazane (HMDS). The amidation reaction may be carried out in the presence of an inert atmosphere at 75 to 150° C., for several hours until the amidation reaction completes.

In yet another embodiment, the step c involves activation of tetrahydrofuroic acid (VI) with an amide such as N-hydroxysuccinimide, asparagine, preferably N-hydroxy succinimide to obtain corresponding ester of formula (VIIc).

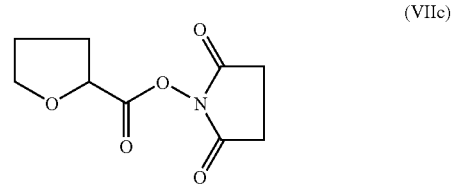 [SMILES: O=C(ON1C(=O)CCC1=O)C1CCCO1]

(VIIc)

The reaction may be carried out in the presence of catalyst such as dimethylaminopyridine, using an organic solvent in an inert atmosphere. The ester (VIIc) is then condensed with diamine (V) in a suitable organic solvent preferably dichloromethane using a suitable organic base or an inorganic base, in an inert atmosphere to form alfuzosin hydrochloride. The condensation reaction may be carried out by isolating intermediate ester (VIIc). In the process of the present invention the reaction is carried out without isolating ester (VIIc).

In yet another embodiment, the present invention provides a novel process for preparing alfuzosin hydrochloride comprising reacting tetrahydrofuroic acid (VI) with ethyl chloroformate in the presence of a suitable base using polar protic solvent and condensing with a solution of diamine (V).

The condensation of compounds (VII) and (V) may involve reacting a solution of compound (VI) or (VII) with diamine compound (V) or vice versa in a solvent at a suitable temperature to yield alfuzosin. After completion of reaction, the mixture may be basified, extracted in a suitable solvent, neutralized, washed with water and dried. In this way, the alfuzosin base is isolated. Alternatively, the solvent, may be evaporated partially or completely to provide a residue or solution of alfuzosin base in a solvent. In this way, the alfuzosin base is not isolated. In a preferred embodiment, a residue of alfuzosin is dissolved in methanol and acidified with hydrochloric acid either as gas or as an aqueous solution or as alcoholic solution.

The solid alfuzosin hydrochloride can be obtained by distilling solvent under reduced pressure, adding antisolvent to the residue of alfuzosin base in a solvent. A suitable antisolvent may be selected from an ester or ether. The alfuzosin hydrochloride can be isolated by filtration and may be purified further by using known crystallization techniques.

Still another aspect of the present invention is to provide a pharmaceutical composition containing a therapeutically effective amount of pure alfuzosin hydrochloride, along with one or more pharmaceutically acceptable carriers, diluents and excipients. Such pharmaceutical compositions and carriers, diluents and excipients are well known to those skilled in the art.

EXAMPLES

The following examples further illustrate the preparation of alfuzosin hydrochloride using the improved process provided by the present invention and are not intended to limit the scope of the present invention in any way.

Example 1

Preparation of N-(4-amino-6,7-dimethoxyquinazol-2-yl)-N-methyl-2-cyanoethylamine hydrochloride 50 gms, 0.208 moles of 4-amino-2-chloro-6,7-dimethoxyquinazoline and 21.2 gms, 0.252 moles of 3-methylaminopropionitrile were charged in a round bottom flask containing 350 ml dimethylformamide. The reaction mass was stirred at about 100° C. for 6 hours, cooled to 25° C. and charged with 250 ml isopropanol. The reaction mass was further stirred for 15 minutes, filtered and washed with 50 ml isopropanol and subjected to drying at 50° C. for 7-8 hours to yield N-(4-amino-6,7-dimethoxyquinazol-2-yl)-N-methyl-2-cyanoethylamine hydrochloride (50 gms).

50 gms of N-(4-amino-6,7-dimethoxyquinazol-2-yl)-N-methyl-2-cyanoethylamine hydrochloride was further purified by heating to reflux in 500 ml methanol for 30 minutes; then cooling to 25° C., filtering, washing with 250 ml methanol and drying under suction. The compound was dried under vacuum at 50° C. for 5 hours. Yield—42 gms. (62%.)

Example 2

Preparation of N-(4-amino-6,7-dimethoxyquinazol-2-yl)-N-methyl-2-cyanoethylamine hydrochloride 50 gms, 0.208 moles of 4-amino-2-chloro-6,7-dimethoxyquinazoline and 21.2 gms, 0.252 moles of 3-methylaminopropionitrile were charged in a round bottom flask containing 350 ml hexamethylphosphoramide. The reaction mass was stirred at about 100° C. for 9 hours, cooled to a temperature of 25° C. and then charged with 250 ml isopropanol. The reaction mass was further stirred for 15 minutes, filtered and washed with 50 ml isopropanol and subjected to drying at 50° C. for 7-8 hours to yield N-(4-amino-6,7-dimethoxyquinazol-2-yl)-N-methyl-2-cyanoethylamine hydrochloride (43 gms).

43 gms of N-(4-amino-6,7-dimethoxyquinazol-2-yl)-N-methyl-2-cyanoethylamine hydrochloride was further purified by heating to reflux in 500 ml methanol for 30 minutes; then cooling to 25° C., filtering, washing with 250 ml methanol and drying under suction. The compound was dried under vacuum at 50° C. for 5 hours. Yield—30 gms. (44.42%)

Example 3

Preparation of N-(4-amino-6,7-dimethoxyquinazol-2-yl)-N-methyl-2-cyanoethylamine hydrochloride 100 gms, 0.417 moles of 4-amino-2-chloro-6,7-dimethoxy quinazoline and 45.6 gms, 0.542 moles of 3-methyl amino propionitrile were charged in a round bottom flask containing 1000 ml diglyme and 100 ml t-butanol. The reaction mass was stirred at about 125° C. for 7 hours. The reaction mass was cooled to a temperature of 25° C., was further stirred for 1 hour, filtered and washed with 100 ml isopropanol.

The solid obtained was further refluxed in 1000 ml methanol for 30 minutes, then cooled to 25° C., stirred for 1 hour at 25° C., filtered, washed with 200 ml methanol and dried under suction. The compound N-(4-amino-6,7-dimethoxyquinazol-2-yl)-N-methyl-2-cyanoethylamine hydrochloride was dried under vacuum at 50° C. for 5 hours. Yield—102 gms. (75.55%).

Example 4

Preparation of N-(4-amino-6,7-dimethoxyquinazol-2-yl)-N-methylpropylenediamine hydrochloride 100 gms, 0.309 moles of N-(4-amino-6,7-dimethoxyquinazol-2-yl)-N-methyl-2-cyanoethylamine hydrochloride, 100 gms of Raney-Nickel and 1250 ml of solution of 6.9% ammonia in denatured spirit (denatured ethanol) were charged in an autoclave.

The reaction mixture was hydrogenated at 70° C. under a pressure of 5 kg/cm$^2$ (70 psi) for 2 hours. The reaction mass was cooled to room temperature and filtered on hyflo bed. The solvent was distilled under reduced pressure. The residue obtained was stirred in 250 ml acetonitrile at 45-50° C., filtered and concentrated under reduced pressure at 60° C. The residue was dissolved in 250 ml isopropanol and acidified to pH 1-2 with isopropanolic HCl. The N-(4-amino-6,7-dimethoxyquinazol-2-yl)-N-methylpropylenediamine hydrochloride obtained was isolated by filtration and dried under vacuum at 60° C. for 8 hours. Yield—109 gms

Example 5

Preparation of N-(4-amino-6,7-dimethoxyquinazol-2-yl)-N-methylpropylenediamine hydrochloride 50 gms, 0.154 moles of N-(4-amino-6,7-dimethoxyquinazol-2-yl)-N-methyl-2-cyanoethylamine hydrochloride, 50 gms Raney-Nickel, 600 ml aqueous ammonia solution and 400 ml denatured spirit (denatured ethanol) were charged in an autoclave.

The reaction mixture was hydrogenated at 70° C. under a pressure of 5 kg/cm$^2$ (70 psi) for 2 hours. The reaction mass was cooled to room temperature and filtered on hyflo bed. The solvent was distilled under reduced pressure. The residue obtained was stirred in 125 ml acetonitrile at 45-50° C., filtered and concentrated under reduced pressure at 60° C. The residue was dissolved in 150 ml isopropanol and acidified to pH 1-2 with isopropanolic HCl. The N-(4-amino-6,7-dimethoxyquinazol-2-yl)-N-methylpropylenediamine hydrochloride obtained was isolated by filtration and dried under vacuum at 60° C. for 8 hours. Yield—27.5 gms. (54.33%)

Example 6

Preparation of N-(4-amino-6,7-dimethoxyquinazol-2-yl)-N-methylpropylenediamine hydrochloride 25 gms, 0.77 moles of N-(4-amino-6,7-dimethoxyquinazol-2-yl)-N-methyl-2-cyanoethylamine hydrochloride, 25 gms of Raney-Nickel and 500 ml of 9.8% methanolic ammonia solution were charged in an autoclave. The reaction mixture was hydrogenated at 70° C. under a pressure of 5 kg/cm$^2$ (70 psi) for 2 hours. The reaction mass was cooled to room temperature, filtered on hyflo bed and washed with 200 ml methanol. The solvent was distilled under reduced pressure. The residue obtained was stirred in 50 ml methylene chloride and concentrated under reduced pressure at 40° C. The residue was dissolved in 200 ml isopropanol and acidified to pH 1-2 with isopropanolic HCl. The N-(4-amino-6,7-dimethoxyquinazol-2-yl)-N-methyl propylenediamine hydrochloride obtained was isolated by filtration and dried under suction.

The wet solid was refluxed in 300 ml acetone for 15 minutes, cooled to room temperature, filtered, washed with 50 ml acetone. N-(4-amino-6,7-dimethoxyquinazol-2-yl)-N-methyl propylenediamine hydrochloride was dried under vacuum at 60° C. for 8 hours. Yield—22.7 gms. (89.72%)

Example 7

Preparation of Alfuzosin Hydrochloride Using Thionyl Chloride a) Preparation of Acid Chloride 7.8 gms of tetrahydrofuroic acid and 50 ml toluene were charged in a dry flask under nitrogen. 8.7 gms of thionyl chloride were added dropwise at 25-30° C. The reaction mass was stirred for 1 hour.

b) 13 gms of N-(4-amino-6,7-dimethoxyquinazol-2-yl)-N-methyl propylenediamine hydrochloride, 65 ml toluene and 12.5 ml triethylamine were charged in another dry flask under an inert atmosphere.

c) Acid chloride solution prepared in a) was added to solution b) at 25-30° C. The reaction mass was stirred for 1 hour. The solvent was distilled out completely under reduced pressure. The residue was partitioned between 50 ml water and 100 ml methylene chloride and basified with 10% sodium bicarbonate solution. The organic layer separated out. The aqueous layer was extracted with 50 ml methylene chloride. The combined organic layers were washed with 50 ml water twice, dried on sodium sulfate and distilled under reduced pressure.

d) Preparation of Alfuzosin Hydrochloride

The residue obtained in c) was dissolved in 50 ml methanol and acidified to pH 1-2 with isopropanolic HCl. The solvent was distilled under vacuum and stripped out with 50 ml acetone. The residue was stirred in 50 ml acetone for 1 hour at 25-30° C. The solid was filtered and washed with 10 ml acetone. The solid was dried under vacuum at 60° C. to yield 6.3 gms of alfuzosin hydrochloride. (37.34%)

This example illustrates the preparation of alfuzosin hydrochloride without isolation of alfuzosin base.

Example 8

Preparation of Alfuzosin Hydrochloride Using HMDS

HMDS (42.16 ml, 0.199 moles) was charged in a 100 ml round-bottom flask under argon at room temperature. After cooling to 10° C., tetrahydrofuran-2-carboxylic acid (3.98 gms, 0.0343 moles) was added drop wise and the reaction mass was stirred and heated to 50-55° C. After 5 hours of stirring, the reaction mass was cooled to 0-5° C. and N-(4-amino-6,7-dimethoxyquinazol-2-yl)-N-methylpropylenediamine (10 gms, 0.0343 moles) was added drop wise maintaining temperature below 5° C. The reaction mass was heated to 110° C. After 10 hours, the completion of the reaction was detected by thin-layer chromatography (TLC). After cooling to room temperature, the product was dissolved in dichloromethane, acidified with 6N hydrochloric acid and extracted in 50 ml water. The aqueous layer was washed with dichloromethane and cooled to 10-15° C. The pH of the aqueous layer was adjusted to 10-10.5 with 2N sodium hydroxide solution and the product extracted with 100 ml MDC twice. The organic layer was washed with brine and charcoalized in 5% charcoal. The reaction mass was heated to reflux for 30 mins, filtered hot on hyflo bed and washed bed with 20 ml MDC. The clear MDC layer was dried on sodium sulfate and distilled completely under reduced pressure to obtain residue.

The residue was dissolved in 50 ml methanol, acidified to pH 2-3 with IPA-HCl at room temperature. The solvent was removed under reduced pressure, 50 ml acetone charged, heated to reflux and cooled to room temperature. The solids were filtered and dried under vacuum at 60° C. to yield 9.5 gms of alfuzosin hydrochloride. (73.24%)

This example illustrates the preparation of alfuzosin hydrochloride without isolation alfuzosin base.

It will be appreciated that the invention may be modified within the scope of the appended claims.

The invention claimed is:

1. A process for preparing alfuzosin or a salt thereof comprising:
   (a) condensing 4-amino-2-chloro-6,7-dimethoxyquinazoline (II) with 3-methylaminopropionitrile (III) in the presence of (i) a polar aprotic solvent selected from the group consisting of: diglyme, dimethyl formamide, hexamethylphosphoramide, and mixtures thereof, or (ii) a mixture of a polar aprotic solvent in combination with t-butanol, to form N-(4-amino-6,7-dimethoxyquinazol- 2-yl)-N-methyl-2-cyanoethylamine (IV), wherein the condensation reaction is carried out in the absence of a base;

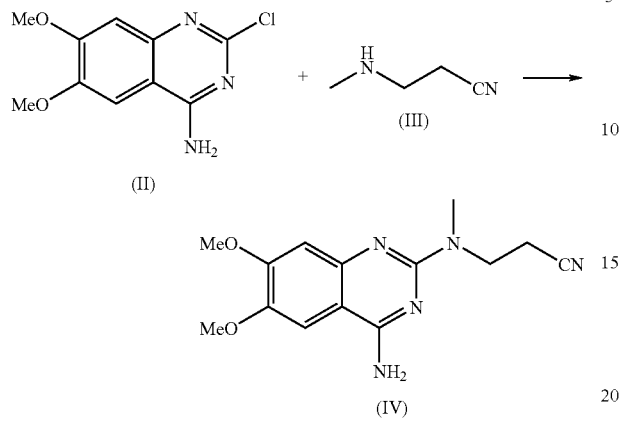

(b) hydrogenating the N-(4-amino-6,7-dimethoxyquinazol-2-yl)-N-methyl-2-cyanoethylamine (IV) using a hydrogenating agent under a pressure of less than 10 kg/cm$^2$ to form N-(4-amino-6,7-dimethoxyquinazol-2-yl)-N-methylpropylenediamine (V) and optionally converting the N-(4-amino-6,7-dimethoxyquinazol-2-yl)-N-methylpropylenediamine (V) to an acid addition salt thereof, wherein the hydrogenation is carried out in the presence of an alcohol and an aqueous ammonia solution;

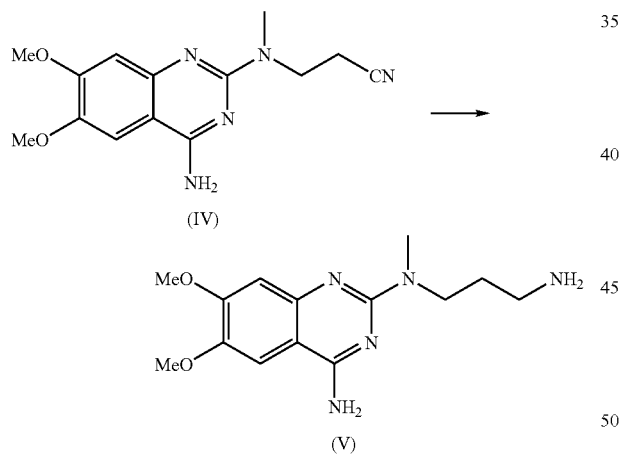

and (c) converting tetrahydrofuroic acid (VI) to an intermediate form (VII)

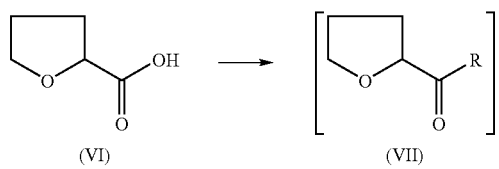

and condensing the intermediate form (VII) with the N-(4-amino-6,7-dimethoxyquinazol-2-yl)-N-methylpropylenediamine (V) or with the acid addition salt thereof to yield alfuzosin base, and optionally converting alfuzosin base to a salt of alfuzosin, wherein R is: (i) a halo group; (ii) OR$_1$ wherein R$_1$ is a silyl group of the formula

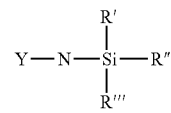

wherein the silyl group is nitrogen bonded to the oxygen of the OR$_1$ group, and wherein R', R" and R'" are the same or different and are selected from hydrogen, optionally substituted C$_1$-C$_6$ alkyl and optionally substituted C$_2$-C$_6$ alkenyl; Y is selected from hydrogen, C$_1$-C$_6$ alkyl, C$_2$-C$_6$ alkenyl and optionally substituted silyl of the formula —SiH$_3$; (iii) OR$_2$ wherein R$_2$ is a C$_1$ to C$_4$ alkyl group; or (iv) OR$_3$, wherein R$_3$ is either (i) succinimide and intermediate form (VII) is intermediate ester (VIIc)

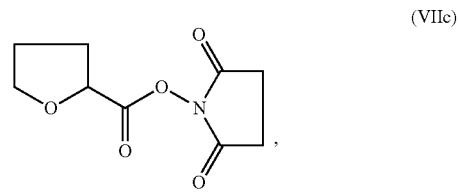 [SMILES: O=C(ON1C(=O)CCC1=O)C1CCCO1]

or (ii) asparagine, wherein the process is carried out without isolating the intermediate of formula (VII).

2. The process according to claim 1, wherein the salt of alfuzosin is the hydrochloride salt.

3. The process according to claim 1, wherein the N-(4-amino-6,7-dimethoxyquinazol-2-yl)-N-methyl-2-cyanoethylamine (IV) is purified prior to hydrogenation by converting the N-(4-amino-6,7-dimethoxyquinazol-2-yl)-N-methyl-2-cyanoethylamine (IV) to a salt thereof.

4. The process according to claim 1, wherein the solvent is diglyme or a mixture of diglyme and t-butanol.

5. The process according to claim 4, wherein the solvent is a mixture of diglyme and t-butanol.

6. The process according to claim 1, wherein the N-(4-amino-6,7-dimethoxyquinazol-2-yl)-N-methyl-2-cyanoethylamine (IV) is converted into an acid addition salt of the formula (IVa) in the presence of an acid HA

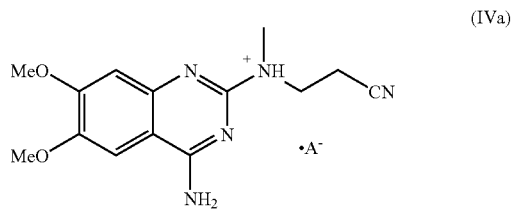

wherein A$^-$ is an anion.

7. The process according to claim 6, wherein the acid is an inorganic acid or organic acid.

8. The process according to claim 7, wherein the acid is hydrochloric acid.

9. The process according to claim 1, wherein the hydrogenating agent is Raney Nickel.

10. The process according to claim 1, wherein the pressure ranges from 5 to 6 kg/cm$^2$.

11. The process according to claim 1, wherein the N-(4-amino-6,7-dimethoxyquinazol-2-yl)-N-methyl propylenediamine (V) is converted to an acid addition salt (Va) in the presence of an acid HA

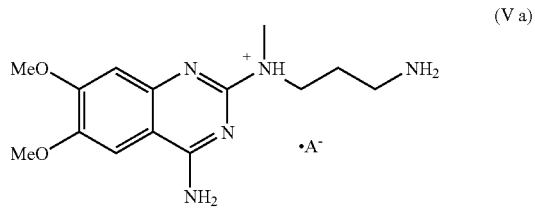

(Va)

wherein A$^-$ is an anion.

12. The process according to claim 11, wherein the acid is an inorganic acid or organic acid.

13. The process according to claim 12, wherein the acid is hydrochloric acid.

14. The process according to claim 1, wherein R is a chloro group and step (c) comprises treating tetrahydrofuroic acid (VI) with a chlorinating agent to yield tetrahydrofuroyl chloride (VIIa)

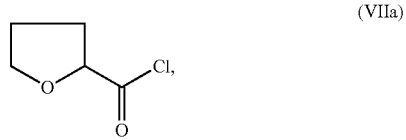

(VIIa)

15. The process according to claim 14, wherein the chlorinating agent is selected from the group consisting of thionyl chloride, phosphorus oxychloride, phosphorus trichloride, phosphorus pentachloride, phosgene and oxalyl chloride.

16. The process according to claim 15, wherein the chlorinating agent is thionyl chloride.

17. The process according to claim 14, wherein, after formation of intermediate (VIIa), unreacted chlorinating agent is removed prior to addition of the diamine (V).

18. The process according to claim 14, wherein a base is present in the reaction mass.

19. The process according to claim 1, wherein R is OR$_1$ and step (c) comprises reacting tetrahydrofuroic acid (VI) with N-(4-amino-6,7-dimethoxyquinazol-2-yl)-N-methylpropylenediamine (V) in the presence of a silicon amine, wherein the silicon amine is selected from 1,1,1,3,3,3-hexamethyldisilazane (HMDS), an alkali metal disilazane or an alkali metal monosilazane.

20. The process according to claim 19, wherein the alkali metal is selected from lithium, sodium or potassium.

21. The process according to claim 19, wherein the silicon amine is 1,1,1,3,3,3-hexamethyldisilazane (HMDS).

22. The process according to claim 1, wherein the alfuzosin base is isolated.

23. The process according to claim 22, wherein the isolated alfuzosin base is converted to alfuzosin hydrochloride.

24. The process according to claim 1, wherein alfuzosin base is not isolated.

25. The process according to claim 24, wherein a residue or solution of alfuzosin base is used directly from the condensation reaction to form alfuzosin hydrochloride.

26. The process according to claim 25, wherein the residue of alfuzosin is dissolved in methanol and acidified with hydrochloric acid either as gas or as an aqueous solution or as alcoholic solution to yield alfuzosin hydrochloride.

27. The process according to claim 1, wherein condensing is carried out in the presence of the mixture of the aprotic solvent and t-butanol.

* * * * *

UNITED STATES PATENT AND TRADEMARK OFFICE
CERTIFICATE OF CORRECTION

PATENT NO. : 8,716,476 B2  Page 1 of 1
APPLICATION NO. : 12/671418
DATED : May 6, 2014
INVENTOR(S) : Kankan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 217 days.

Signed and Sealed this

Twenty-ninth Day of September, 2015

Michelle K. Lee
*Director of the United States Patent and Trademark Office*